United States Patent
McGoff et al.

(10) Patent No.: US 6,706,773 B1
(45) Date of Patent: Mar. 16, 2004

(54) PROCESS FOR PREPARING A FOAM COMPONENT

(75) Inventors: Matthew Grady McGoff, Newcastle Upon Tyne (GB); Scott Edward Stephans, Newcastle Upon Tyne (GB); Hossam Hassan Tantawy, Morpeth (GB); Christopher Charles Driffield, Newcastle Upon Tyne (GB)

(73) Assignee: The Procter & Gamble Company, Cincinnati, OH (US)

( * ) Notice: Subject to any disclaimer, the term of this patent is extended or adjusted under 35 U.S.C. 154(b) by 125 days.

(21) Appl. No.: 10/089,352
(22) PCT Filed: Oct. 4, 2000
(86) PCT No.: PCT/US00/27331
§ 371 (c)(1),
(2), (4) Date: Mar. 27, 2002
(87) PCT Pub. No.: WO01/24990
PCT Pub. Date: Apr. 12, 2001

(30) Foreign Application Priority Data

| Oct. 5, 1999 | (GB) | 9923344 |
| Oct. 5, 1999 | (GB) | 9923393 |
| May 3, 2000 | (GB) | 0010599 |
| Sep. 13, 2000 | (GB) | 0022499 |

(51) Int. Cl.$^7$ .................... C08J 9/00
(52) U.S. Cl. ............. 521/82; 264/45.9; 264/46.1; 264/46.8; 264/142; 424/65; 424/69; 424/400; 424/401; 424/466
(58) Field of Search ............... 521/82; 264/45.9, 264/46.1, 46.9, 142; 424/65, 69, 400, 401, 466

(56) References Cited

U.S. PATENT DOCUMENTS 3,887,614 A 6/1975 Susumu et al.

FOREIGN PATENT DOCUMENTS

GB 972 851 A 10/1964

OTHER PUBLICATIONS

Catalysts Des Techn Bur, Database WPI, Section Ch, Week 199248, Derwent Pub., London, GB; An 1992–39689 XP002156450.

*Primary Examiner*—Morton Foelak
(74) *Attorney, Agent, or Firm*—Caroline Wei-Berk; Kim W. Zerby; Steve W. Miller

(57) ABSTRACT

The present invention relates to a process for preparing a foam component, said process comprises the steps of extruding a viscous mixture from a rotating extrusion plate onto a receiving surface. Said process provides a convenient, efficient, simple means of preparing foam components, especially foam components suitable for use in cleaning compositions. The present invention also provides a foam component obtainable therefrom.

16 Claims, No Drawings

PROCESS FOR PREPARING A FOAM COMPONENT

TECHNICAL FIELD OF THE INVENTION

The present invention relates to a process for preparing foam components and to foam components obtainable therefrom, said process is especially applicable for preparing a foam component which are useful in cleaning compositions such as laundry cleaning compositions.

BACKGROUND TO THE INVENTION

Compositions such as cleaning products and personal care products, cosmetic products and pharmaceutical products, often comprise active ingredients which are to be delivered to water or which are required to be active in an aqueous environment. Many of these active ingredients are sensitive to moisture, temperature changes, light and/or air during storage.

Another problem with many of these active ingredients, in particular enzymes, is that they tend to form dust due to physical forces directed upon them during handling. This not only creates waste product, but the dust can also cause hygiene and health problems.

Attempts to overcome these problems have led to the development of protecting these active ingredients by coating agents or encapsulating agents. Typically these active ingredients are prepared by spraying a coating material onto a core particle comprising the active ingredient to be protected. This process is extremely costly, time-consuming and technically difficult to perform.

The inventors herein provide a process for preparing foam components that are impact robust and do not form dust when acted upon by physical forces typically encountered during handling. The process of the present invention prepares foam components in a single step, thus negating the need for numerous process steps, such as spheronisation.

Said process provides a fast, simple, convenient, and cost effective means of providing a foam component, especially spherical foam components.

The foam components obtainable by the process of the present invention are more impact robust and do not form dust when acted upon by physical forces typically encountered during handling.

SUMMARY OF THE INVENTION

The present invention provides a process for preparing a foam component, said process comprises the steps of extruding a viscous mixture through an aperture of a rotating extrusion plate, onto a receiving surface, and wherein a gas is incorporated into said viscous mixture either prior to, simultaneous to, or subsequent to, said viscous mixture being extruded through said aperture.

Preferably, the shortest distance between said extrusion plate and said receiving surface is from 50 micrometers to 3000 micrometers, and preferably the aperture is of a size of from 50 micrometers to 3000 micrometers.

The present invention also provides foam component obtainable therefrom.

DETAILED DESCRIPTION OF THE INVENTION

Process of Preparing Foam Component

The process of the present invention; herein referred to as "process", provides a simple, fast, efficient, cost-effective means of preparing foam components, especially foam components for use in cleaning compositions. Said foam component is described in more detail hereinafter.

The process herein comprises the steps of extruding a viscous mixture through an aperture of a rotating extrusion plate, onto a receiving surface, and wherein a gas is incorporated into said viscous mixture either prior to, simultaneous to, or subsequent to, said viscous mixture being extruded through said aperture.

Preferably, the shortest distance between said extrusion plate and said receiving surface is from 50 micrometers to 3000 micrometers, and preferably the aperture is of a size of from 50 micrometers to 3000 micrometers.

It may be preferred that the process, especially the step of extruding the viscous mixture through the aperture, is carried out at a temperature of from −20° C. to 100° C., preferably from −10° C., or from 0° C., or from 10° C., and preferably to 90° C., or to 80° C., or to 70° C., or to 60° C., or to 50° C., or to 40° C. If the foam component comprises an ingredient, such as an active ingredient, which is sensitive to temperature, then it is preferred to perform the process at a temperature which is compatible with said temperature sensitive ingredient. For enzyme containing foam components, this temperature is typically from 0° C. to 50° C., preferably from 10° C. to 30° C.

Viscous Mixture

The viscous mixture, herein refereed to as "mixture", typically has a viscosity of from 1 mPas to 200000 mPas. The mixture herein is preferably a fluid or liquid. The viscosity of the mixture depends on the chemical and physical properties of the ingredients in the mixture, which typically depends on the ingredients required in the foam component. However, if the viscosity is too low, then the mixture will pour too rapidly through the aperture onto the receiving surface and will not form extruded particles. Conversely, if the mixture is too viscous, then the mixture will either not be able to pass through the aperture, or will form extruded noodles, as opposed to extruded particles, which will require additional cutting steps and possibly spheronisation steps before a useable foam component is prepared.

Typically the viscosity of the mixture is from 2 mPas, or from 5 mPas, or from 7 mPas, or from 10 mPas, or from 12 mPas, or from 15 mPas, or from 17 mPas, or from 20 mPas, or from 22 mPas, or from 25 mPas, or from 50 mPas, or from 100 mPas, or from 150 mPas, or from 200 mPas, and typically to 150000 mPas, or to 100000 mPas, or to 50000 mPas, or to 25000 mPas, or to 12000 mPas, or to 10000 mPas, or to 8000 mPas, or to 50000 mPas.

The mixture typically comprises all or most of the ingredients that will be present in the foam component. Typically the mixture comprises a polymeric material, a plasticiser and an active ingredient, and preferably also comprises a stabilising agent, a dissolution aid. Said polymeric material, plasticiser, active ingredient, stabilising agent, dissolution aid are described in more detail herein after.

The water content of the mixture affects the physical and chemical properties of the mixture. Typically, the water content of the mixture is from 0.1 wt % to 80 wt %, preferably from 60 wt % to 80 wt %. If the mixture comprises ingredients especially active ingredients, which are sensitive to water, for example ingredients which degrade in the presence of water, then it is preferred that the water content of the mixture is as low as possible, possibly being less than 5 wt %, or less than 3 wt %, or less than 1 wt %, or less than 0.1 wt %, or it may even be preferred that the mixture is free from water. The term "water" typically means water molecules which are not bound to other compounds, for example, the term "water" typically does not include the water content of hydrated molecules such as aluminosilicate but does include water added to the mixture, for example as a processing aid.

Alternatively, it may be preferred for the mixture to comprise water. For example, if the mixture comprises a polymeric material, it may be preferred for water to be also be present in the mixture to act as a plasticiser when forming a foam component from said polymeric material. If water is present in the mixture, then preferably said water is present at a level of at least 3 wt %, or at least 5 wt %, or at least 10 wt %, or at least 20 wt % or even at least 40 wt %.

The presence of solid matter in said mixture affects the extrusion process and the subsequent extruded particle formation. The extrusion of said liquid is typically more difficult when undissolved solid matter is present in said mixture. Furthermore, the extruded particle formed by extruding a mixture comprising undissolved solid matter typically requires additional processing steps such as spheronisation. Therefore, preferably the mixture preferably comprises (by weight) less than 30%, preferably less than 15%, preferably less than 12%, preferably less than 10%, preferably less than 7%, preferably less than 5%, preferably less than 3%, preferably less than 1%, preferably less than 0.1% undissolved solid matter. Most preferably, the mixture comprises no undissolved solid matter. Typically the levels of undissolved solid matter described above refer to the amount of solid matter during the step of extruding said mixture through an aperture of a rotating extrusion plate and onto a receiving surface. It may be preferred for the mixture to comprise solid matter during the process of the present invention other than during the extrusion step.

If undissolved solid matter is present during the extrusion step, then preferably the solid matter is in the form of undissolved particles having a particle size smaller than, and thus being able to pass through, an aperture of a size of from 50 micrometers to 3000 micrometers, or other preferred sizes of said aperture which are described in more detail hereinafter.

Rotating Extrusion Plate

The rotating extrusion plate preferably rotates at from 1 rpm to 1000 rpm, preferably from 2 rpm, or from 3 rpm, or from 4 rpm, or from 5 rpm, or from 6 rpm, or from 7 rpm, or from 8 rpm, or from 9 rpm, or from 10 rpm, and preferably to 900 rpm, or to 800 rpm, or to 700 rpm, or to 600 rpm, or to 500 rpm, or to 400 rpm, or to 300 rpm, or 200 rpm, or to 100 rpm, or to 50 rpm. The rotating extrusion plate may rotate in a clockwise or anti-clockwise direction.

The rotating extrusion plate typically has a tip speed of from 0.1 $ms^{-1}$ to 1600 $ms^{-1}$, or typically from 10 $ms^{-1}$, or from 50 $ms^{-1}$, or from 100 $ms^{-1}$, or from 150 $ms^{-1}$, or from 200 $ms^{-1}$, and typically to 900 $ms^{-1}$, or to 800 $ms^{-1}$, or to 700 $ms^{-1}$, or to 600 $ms^{-1}$, or to 500 $ms^{-1}$, or to 400 $ms^{-1}$. For the purpose of the present invention, the tip speed of the rotating extrusion plate is typically defined as the angular velocity of the outer surface, or outer edge, of said rotating extrusion plate.

The direction of rotation, or typically the angular direction of rotation, of the rotating extrusion plate is typically perpendicular like, or perpendicular to, the direction of flow of the viscous liquid through the aperture of the rotating extrusion plate.

The rotating extrusion plate is typically a housing enclosing, or at least partially enclosing a volume capable of holding the liquid prior to the extrusion step. The housing rotates around said volume, in a clockwise or anti-clockwise manner. This housing can be a single layer of housing or can be more than one layer of housing, for example an outer layer and an inner layer. For the purposes of the present invention, if the rotating extrusion plate is in the form of a housing for a volume, and said housing contains more than one layer, then only one layer needs to rotate, although it may be preferred for more than one layer, or even all of the layers of the housing, to rotate. If the housing consists of an outer layer and an inner layer, then preferably the outer layer rotates, although the inner layer may rotate, or even both the inner layer and the outer layer rotate.

Preferably, the rotating extrusion plate is cylindrical, spheroid, or cubic in shape. The rotating extrusion plate may be a polyhedral shape, such as a tetrahedral, pentahedral, hexahedron, rhombohedral, heptahedral, octahedral, nonahedral, decahedral, Most preferably, the rotating expansion plate is cylindrical such as a barrel shape.

The rotating extrusion plate comprises an aperture of a size of from 50 micrometers to 3000 micrometers, preferably from 100 micrometers to 1000 micrometers. These apertures are typically formed by laser cutting the extrusion plate. Typically, said rotating extrusion plate comprises more than one aperture, preferably numerous apertures. If the rotating extrusion plate comprises more than one aperture, then said apertures may be a different size. By differing the sizes of the apertures and number of apertures having the same size, the size distribution of the extruded particle can be controlled, and extruded particles having a desired particle size distribution can be obtained from the process herein.

Typically the density of apertures present on said rotating extrusion plate is from 0.001 $mm^{-2}$ to 400 $mm^{-2}$, or from 0.1 $mm^{-2}$, or from 0.1 $mm^{-2}$, or from 1 $mm^{-2}$, or from 5 $mm^{-2}$, or from 10 $mm^{-2}$, or from 25 $mm^{-2}$, or from 50$mm^{-2}$, or from 100 $mm^{-2}$, and preferably to 300 $mm^{-2}$, or to 275 $mm^{-2}$ or to 250 $mm^{-2}$, or to 225 $mm^{-2}$, or to 200 $mm^{-2}$, or to 175 $mm^{-2}$, or to 150 $mm^{-2}$. Different areas of the rotating extrusion plate may have a different density of apertures present in said area. For example, smaller size apertures may be present in a higher density in one area of the rotating extrusion plate, whilst larger size apertures may be present in a lower density on a different area of said rotating extrusion plate.

If it is preferred that the process of the present invention prepares a spherical foam component, then the aperture preferably has a shape which resembles, or is, a square, rectangle, rhombus, triangle, oval, circle or diamond, preferably diamond. If more than one aperture is used in the present invention, then more than one type of shape of aperture may be used.

It may be preferred that the rotating extrusion plate is at least partially coated, preferably completely coated, with a release agent. The release agent acts to reduce the adhesive properties between the surface of the rotating extrusion plate and the liquid, thus the release of said liquid from the rotating extrusion plate, especially during the extrusion step. Typical release agents comprise hydrophobic material such as wax, oil, grease, combinations thereof, preferably silicone oil.

The rotating extrusion plate may also be coated by agents which reduce the interaction between the rotating extrusion plate and the liquid or part thereof. Preferred coatings are plasma coating, polish finishes, or a combination thereof. These coatings may be in addition to a coating comprising release agent, or may be in combination with the coating of release agent. Preferred plasma coatings comprise polyethylene, polypropylene, or a combination thereof. Typical plasma coatings comprise components known under the trade name as Teflon.

If the rotating extrusion plate is a housing for a volume capable of holding the liquid, then it may be preferred that both the inner surface or outer surface is coated, or partially coated, with the release agent and/or other coating such as a plasma coating. If the rotating extrusion plate is a housing which comprises more than one layer, then it may be preferred for any layer or part thereof to be coated, or partially coated, with release agent and/or other coating such as plasma coating.

More than one rotating extrusion plate may be used in the process of the present invention, although it is preferred that only one rotating extrusion plate is used herein.

Preferred rotating extrusion plates for use herein are those known under the trade names as Rotoform supplied by Sandvik Conveyor GMBH, and Disk Pastillator supplied by Gausche Machinefabriek.

Extrusion of Viscous Mixture

The mixture is extruded from a rotating extrusion plate through an aperture onto a receiving surface. The temperature of this process step is preferably as described above.

Typically, the mixture is forced by a forcing means through the aperture. The force required to extrude the mixture through the aperture depends on the size of the aperture, the temperature of said extrusion step, and the physical and chemical properties of said mixture, such as viscosity. The forcing means can comprise pushing, scraping, sucking the liquid through the aperture. The forcing means can be in the form of a solid object, such as a bar, wedge, scraper, or combination thereof, which scrapes or pushes the mixture through the aperture. The forcing means may also be a pump, which pumps the mixture through the aperture. A combination of a pump and one or more means selected from a bar, wedge or scraper may also be used herein.

The mixture is typically extruded through the aperture in the form of a extrudate droplet. Said droplet is typically forced onto the receiving surface by said forcing means The rotation of the extrusion plate typically pulls the droplet apart, leaving part of said droplet on the receiving surface to form an extruded particle. The force required to pull the extruded droplet apart must be greater than the yield strength of said droplet.

Receiving Surface

The receiving surface typically receives the extrudate from the rotating extrusion plate, upon which said extruded liquid forms an extruded particle.

The receiving surface can be a belt, a drum, a disc, a platen, or a shape similar or identical to the rotating extrusion plate. Preferably the receiving surface is a belt or disk. Even more preferably the receiving surface is a conveyor belt or spinning disk.

The shortest distance between the receiving surface and the rotating extrusion plate at is from 50 micrometers to 3000 micrometers. For the purpose of the present invention, the shortest distance means the distance measured at the closest point of proximity. Preferably, this distance is the height or cross-sectional distance, of the foam component prepared by the process herein. For example, if a spherical foam component having a mean diameter of 200 micrometers is required, then the preferred shortest distance between the rotating extrusion plate and the receiving surface is 200 micrometers.

The receiving surface may rotate, said rotation may be clockwise or anti-clockwise. Preferably the receiving surface rotates counter-clockwise to the rotating extrusion plate. For example, if the rotating extrusion plate rotates in a clockwise direction, then the receiving surface preferably rotates in an anti-clockwise direction. This prevents the extruded particles and/or liquid smearing or being damaged by the rotating extrusion plate when positioned on the receiving surface.

The receiving surface can be maintained at any temperature as required, this can include heating or cooling said receiving surface. Preferably, the receiving surface is at a temperature of from −20° C. to 200° C., preferably from −10° C., or from 0° C., or from 10° C., or from 20° C., and preferably to 150° C., or to 100° C., or to 99° C., or to 75° C., or to 60° C. or to 50° C., or to 40° C., or to 30° C. Different areas of the receiving surface can be at different temperatures if required. For example, a first area of the receiving surface can be at a higher temperature than a second area.

It may be preferred that the receiving surface is coated, or at least partially coated, with release agents or other coatings such as plasma coating or polish finishes. Said coatings and release agents are described hereinbefore. If said receiving surface is coated, or partially coated, with a release agent, then not only are the adhesive properties between the receiving surface and the extruded particle reduced, allowing easier release of said extruded particle from said receiving surface, but in addition to this, the surface tension between the extruded particle and the receiving surface is increased, thus reducing the area of contact between the extruded particle and the receiving surface and as a consequence of this, the extruded particle is more spherical in shape.

Incorporation of Gas

Gas is incorporated into the liquid by any suitable means. The gas is incorporated into said mixture either prior to, simultaneous to, or subsequent to said mixture being extruded through said aperture. Preferably, the gas is incorporated into said mixture prior to said mixture being extruded through the aperture of a rotating extrusion plate.

The incorporation of gas into said mixture causes said mixture to foam.

Typically this is by physical and/or chemical introduction of said gas into said mixture. Preferred methods are;

(a) gas injection (dry or aqueous route), optionally under mixing, high shear mixing (dry or aqueous route), gas dissolution and relaxation including critical gas diffusion (dry or aqueous route), injection of a compressed gas such as a super critical fluid; and/or (b) chemical in-situ gas formation, typically via a chemical reaction(s) of one or more ingredients including formation of $CO_2$ by an effervescence system; and/or (c) steam blowing, UV light radiation curing.

The gas preferably comprises $CO_2$, $N_2$, or a combination thereof such as air. The gas may also be a compressed gas such as a super critical fluid.

If said gas is incorporated in the mixture prior to said mixture being extruded thorough an aperture, then preferably if the gas forms bubbles in said mixture, these bubbles are smaller than the aperture which the mixture is extruded through.

Foam Component

The foam component is formed by extruding a mixture through an aperture of a rotating extrusion plate, onto a receiving surface. Typically, the foam component is formed as an extruded particle on the receiving surface.

The extruded particle can be a liquid, such as a droplet, or can be solid particle such as a bead or tablet. Preferably the extruded particle is a solid and is typically formed from the extruded liquid which dries on the receiving surface.

The foam component can be subjected to further processing steps. For example, the foam component can be transferred from the receiving surface into a fluid bed and dried. The temperature of this fluid bed drying step is typically from 40° C. to 80° C., preferably from 40° C. to 60° C.

The foam component is preferably a sphere or spheroid. This is especially true if the receiving surface is coated or partially coated with release agent such as silicone oil.

The gas that is injected into said mixture, especially if in a compressed state such as a super critical fluid, may return to a gaseous state in the extruded particle and leave holes or gaps in the structure of the extruded particle. This is an important part of the foaming process. It may be preferred for the mixture to be at a high temperature or high pressure prior to being extruded. At these conditions, the gas may be in a compressed form or a super critical fluid. Subsequent to the extrusion step, the extruded particle which is formed from the extruded mixture, may be at a lower temperature and/or pressure such as ambient conditions, and the gas returns to a gaseous state and foams the extrudate. This foaming step may occur on the receiving surface.

The foam component, herein referred to as "component", typically comprises an active ingredient, a matrix and a dissolution aid. Said active ingredient, matrix and stabilising agent are described in more detail hereinafter.

Said component herein is preferably water-dispersible, water-disintegrating or water-soluble. Preferred water-dispersible articles herein have a dispersibility of at least 50%, preferably at least 75% or even at least 95%, as measured by the method set out hereinafter using a glass-filter with a maximum pore size of 50 microns; more preferably the article herein is water-soluble or water-disintegrating and has a solubility or disintegration of at least 50%, preferably at least 75% or even at least 95%, as measured by the method set out hereinafter using a glass-filter with a maximum pore size of 20 microns, namely:

Gravimetric method for determining water-solubility, water-disintegration or water-dispersibility of the component herein:

50 grams ±0.1 gram of the article herein is added in a 400 ml beaker, whereof the weight has been determined, and 245 ml ±1 ml of distilled water is added. This is stirred vigorously on magnetic stirrer set at 600 rpm, for 30 minutes. Then, the article-mixture is filtered through a folded qualitative sintered-glass filter with the pore sizes as defined above (max. 20 or 50 microns). The water is dried off from the collected filtrate by any conventional method, and the weight of the remaining article fraction is determined (which is the dissolved, disintegrated or dispersed fraction). Then, the % solubility, disintegration or dispersibility can be calculated.

The component herein is typically used to deliver actives to aqueous environment. Then, the component herein, and preferably the matrix thereof, is unstable when brought into contact with water. This occurs such that the active ingredient(s) or part thereof, present in the component is delivered to a liquid, preferably an aqueous environment such as water. Preferably the component or part thereof denatures, disintegrates, preferably disperses or dissolves in liquid, preferably in an aqueous environment, more preferably in water. It may be preferred that the active ingredient is delivered rapidly to water and that the component is such that it disperses or dissolves rapidly; preferably at least 10% of the article, by weight, is dissolved or dispersed in 30 minutes after contacting said component with water, or more preferably at least 30% or even at least 50% or even at least 70% or even at least 90% (introduced in the water at a 1% by weight concentration). It may even be preferred that this happens within 20 minutes or even 10 minutes or even 5 minutes after contacting the component with the water. The dissolution or dispersion can be measured by the method described hereinbefore for measuring the dissolution, disintegration and dispersion of the component herein.

Preferably the component is such that the total volume of the component is changed, preferably reduced, with at least 10%, compared to the initial total volume, as for example can be determined when 1 $cm^3$ of the component is added to 100 ml of demineralised water upon and stirred for 5 minutes at a speed of 200 rpm, at a temperature of 25° C. Preferably the change, or preferably reduction, in total volume is at least 20% or even at least 40% or even at least 60% or even at least 90% or even about 100%, e.g. because it may be preferred that substantially the whole component is disintegrated, dispersed or preferably dissolved into the water quickly.

This can be measured by use of any method known in the art, in particular herein with a method as follows (double immersion technique):

1 $cm^3$ of an elastic article is obtained and introduced in a 100 ml micro volumetric measuring cylinder which is filled with 50 ml±0.1 ml of an organic inert solvent. Acetone is for example used when found to be neither denaturing and/or not interacting with the polymeric material in the matrix of the elastic article herein, for example when this is PVA. Other neutral organic medium can be used according to the nature of the article under investigation; the inert solvent is such that the component is substantially not dissolved, dispersed, disintegrated or denatured by the solvent.

The cylinder is air sealed and left to rest for 1 minute so that the solvent penetrates the whole component. The change in volume is measured and taken as the original volume $V_i$ of the foam specimen. The component is then removed from the solvent and left to dry in air so that the solvent evaporates.

The component is then placed in a 250 ml beaker containing 100 ml of demineralised water, maintained at 25° C., under stirring at 200 rpm with the help of a magnetic stirrer, for 5 minutes. The remaining of the component specimen, if any, is filtered off with a 60 mm mesh copper filter and placed in an oven at a temperature and for a period such that residual water is removed. The dried remaining article is re-introduced in the measuring cylinder which volume of acetone had been re-adjusted to 50 ml. The increase in total volume is monitored and taken as the final volume of the component $V_f$. The decrease in total volume $\Delta V$ of the component specimen is then:

$$\%\Delta V = \frac{Vf}{Vi} * 100.$$

The component preferably has a relative density $\rho^*$ of from 0.01 to 0.95, more preferably from 0.05 to 0.9 or even from 0.1 to 0.8 or even form 0.3 to 0.7. The relative density is the ratio of the density of the component ($\rho^*$), to the sum of the partial densities of all the bulk materials used to form component($\rho_s$).

The preferred foamed component as used herein is air-stable or stable upon contact with air, which means herein that the bulk volume of the component or matrix thereof substantially remains the same when exposed to air. This means in particular that the component retains preferably from 75% to 125% or even from 90% to 110% or even from 95% to 100% of its bulk volume when stored in an open beaker (9 cm diameter; without any protective barrier) in a incubator under controlled ambient conditions (humidity= RH 60%, temperature=25° C.) for 24 hours. Preferably the component retains from 75% to 125% or even from 90% to 110% or even from 95% to 100% of its bulk volume under the above storage conditions whereby the humidity is 80%.

The bulk volume change can be measured by any conventional method. In particular useful is a digital image recorder system containing a digital camera coupled to a personal computer itself equipped with calibrated image analyser software. A 1 cm$^3$ specimen of the article is obtained and introduced in an open beaker having a diameter of 9 cm and stored for 24 hours at the above conditions. After 24 hours, the size in all three dimensions is measured with the image analysis recorder system. Each specimen measurement is repeated three times, and the average bulk volume change is calculated in %.

Preferably, the component is such that, when in the form of particles of a mean particle size of 2000 microns or less, these particles also retain from 75% to 125% or even from 90% to 110% or even from 95% to 100% of their bulk volume. This can for example be measured by placing 20 grams of such particles, or a weight comprising more than 500 particles, in a volumetric beaker having a diameter of 9 cm. The beaker is taped lightly on its base until the particles re-arrange themselves in a stable position with a horizontal top surface. The volume is measured. The open beaker with the particles is then carefully placed in the incubator for 24 hours, set to the desired %RH and temperature. The bulk volume after the 24 hours is measured and the change of bulk volume is calculated in %.

The component comprises (by weight) preferably at least 1% active ingredients), more preferably from 5% to 70%, more preferably at least 10% by weight of the article, more preferably from 15% or even 20% or even 25% to 50%.

The component comprises (by weight) preferably from 10% to 99% matrix, more preferably at least 20% or even 30% to 99%, more preferably from 20% or 30% to 90% to 80%.

The component comprises (by weight) at least 1% stabilising agent, more preferably from 5%, or from 10%, or from 15%, or from 20%, and to 50%, or to 40%, or to 30%, or to 25%.

Matrix

The matrix of the component, herein referred to as "matrix", is typically formed form a polymeric material and preferably a plasticiser. Said polymeric material and said plasticiser are described in more detail hereinafter.

The ratio of plasticiser to polymeric material in the matrix is preferably 1 to 100, more preferably 1 to 70 or 1 to 50, more preferably 1 to 30 or even 1 to 20, depending on the type of plasticiser and polymeric material used. For example, when the polymeric material comprises PVA and the plasticiser comprises glycerine or glycerol derivatives and optionally water, the ratio is preferably around 1:15 to 1:8, a preferred ratio being around 10:1.

The matrix herein may further comprise the active ingredient of the component herein and/or the dissolution aid of the component herein. Said active ingredient and said dissolution aid are described in more detail hereinafter. Cross-linking agents may also be added to modify the properties of the matrix or the resulting component as appropriate. Borate may be useful in the matrix herein.

The matrix herein preferably has a glass transition temperature (Tg) of below 50° C., preferably below 40° C., preferably less than 20° C. or even less than 10° C. or even less than 0° C. Preferably the matrix herein has a Tg of above −20° C. or even above −10° C.

The Tg of the matrix when used herein, is the Tg of the matrix as present in the component, which thus may be a mixture of polymeric material and plasticiser alone, or a mixture of polymeric material, plasticiser, active ingredient and/or stabilising agent, and in any case, optional additional ingredients may be present (such as, stability agents, densification aids, fillers, lubricants etc., as described hereinafter).

The Tg as used herein is as defined in the text book 'Dynamic Mechanical Analysis' (page 53, FIG. 3.11c on page 57), as being the temperature of a material (matrix) where the material (matrix) changes from glassy to rubbery, namely where chains gain enough mobility to slide by each other.

The Tg of the matrix of the component of the invention can be measured in the Perkin-Elmer DMA 7e equipment, following the directions in operations manual for this equipment, generating a curve as illustrated in the book Dynamic Mechanical Analysis—page 57, FIG. 3–11c. The Tg is the temperature or log Frequency as measured with this equipment, between the glass and 'leathery region', as defined in that text.

The matrix, and preferably the component as a whole, has a specific elasticity and flexibility, because of its specific glass transition temperature. In particular, this means that the matrix and the component reversibly deform, absorbing the energy of impacts or of forces so that the component or matrix remains substantially its original bulk volume after the physical force seizes to be applied on the component.

The elasticity can be defined by the elastic modulus of the matrix, or even the component, which again can be defined by the Young's modulus. This can be calculated from strain or stress mechanical tests as known in the art, for example by using Perkin-Elmer DMA 7e equipment following the manufacturer's experimental procedure over a specific % static strain range, namely in the range of 10–40% static strain. This represents a maximum strain as could be applicable during normal manufacturing or handling Thus, the elastic modulus as defined herein is the maximum modulus as measured with this equipment in the range of 10% to 40% static strain. For example a piece of matrix (or component) of 1 cm$^3$ can be used in the testing with this equipment.

The matrix herein typically has an elastic modulus or Young's modulus of less than 4 GN.m$^{-2}$, or typically less than 2 GN.m$^{-2}$, even more preferentially less than 1 GN.m$^{-2}$, but typically even less than 0.5 GN.m$^{-2}$, or even less than 0.1 GN.m$^{-2}$, or even less than 0.01 GN.m$^{-2}$, as measured with the Perkin-Elmer DMA 7e equipment. In particular a matrix herein which contains gas bubbles, e.g. formed by processes involving the introduction of air in the matrix, has an elastic modulus below 0.1 $GN.m^{-2}$ or even 0.01 $GN.m^{-2}$ or even below 0.005 $GN.m^{-2}$ or even below 0.0001 $GN.m^{-2}$.

Preferably the matrix is flexible, such that it has a relative yield strain greater than 2%, and preferably greater than 15% or even greater than 50% 1c, as measured with the Perkin-Elmer DMA 7e equipment (The yield strain is in this measurement the limit deformation of a piece of matrix at which the it deforms irreversible).

In particular this means that when a matrix sample having a cross section of a specific length, for example 1 cm, is compressed with a static force applied along the axis of that cross section, the static force being variable but at least equivalent to twice atmospheric pressure, the change of this length after removal of the force is at least 90% to 110% of the original length. This can for example be measured by use of Perkin-Elmer DMA 7e equipment.

Similarly, the matrix is preferably flexible to such an extend that when a matrix sample having a cross section of a specific length, for example 1 cm, is stretched with a static force applied along the axis of that cross section, the static force being variable, but at least equivalent to twice atmospheric pressure, the change of this length after removal of the force is at least 90% to 110% of the original length. This can for example be measured by use of Perkin-Elmer DMA 7e equipment.

In particular, when using this equipment, the static forces applied along the axis of a cross section of a 1 $cm^3$ matrix sample are gradually increased until the deformation of the component, in the direction of the cross section, is 70%. Then, the force is removed and the final deformation of the matrix sample in the direction of the cross section is measured. Preferably, this length of the cross section after this experiment is preferably from 90% to 110% of the original length of the cross section, preferably from 95% to 105% or even from 98% to 100%.

The elastic modulus or Young's modulus is related to the relative density, namely $$\frac{E^*}{E_s} \approx \left(\frac{\rho^*}{\rho_s}\right)^2,$$

where $\rho^*$ is the relative density of the matrix or even the component, and $\rho_s$ is the relative densities of the components of the matrix or component, as described herein, and $E^*$ is the Young's modulus of the matrix or even the component itself, and $E_s$ that of the components of the matrix or even the component. This means that even a stiff polymeric material, with a high $E_s$ can be made into an elastic, flexible matrix by adjusting the levels and/or type of plasticiser and optionally by modifying the density (or for example by introducing gas during the making process to form foam component, as described below).

The matrix, or even the component as a whole, is in the form of a foam and preferably such that it forms an interconnected network of open and/or closed cells, in particular a network of solid struts or plate which form the edges and faces of open and/or closed cells. The spacing inside the cells can contain part of the active ingredient and/or a gas, such as air.

Preferably, the ratio of the closed cells to open cells in the matrix of the component, or the component as a whole is more than 1:1, preferably more than 3:2 or even more than 2:1 or even more than 3:1. This ratio can be determined by calculating the Total Volume of a specimen of the matrix or component, $V_T$, (assuming a spherical shape), and then measuring with a Mercury Porosimetry Test method the Open Cell Volume ($V_O$) and subtracting the Open Cell Volume from the Total Volume should deliver the Closed Cell Volume ($V_C$: $V_T=V_O+V_C$).

Polymeric Material

Any polymeric material can be used to form the matrix herein, preferably the polymeric material has itself a Tg as described above or more typically, it can be formed into a matrix having the Tg as described above by using a suitable amount of plasticiser.

Preferably, the polymer material comprises or consists of amorphous polymer(s).

The polymeric material may consist of a single type of homologous polymer or may be a mixture of polymers. Mixtures of polymers may in particular be beneficial to control the mechanical and/or dissolution properties of the component, depending on the application thereof and the requirements thereof.

Preferred it that the polymeric material comprises a water-dispersible or more preferably a water-soluble polymer. Water-dispersible and water-soluble are typically defined as described hereinbefore, as per the method for determining the water-solubility and water-dispersibility of the component herein. Preferred water-dispersible polymers herein have a dispersibility of at least 50%, preferably at least 75% or even at least 95%, as measured by the method set out hereinbefore using a glass-filter with a maximum pore size of 50 microns; more preferably the polymer herein is a water-soluble polymer which has a solubility of at least 50%, preferably at least 75% or even at least 95%, as measured by the method set out hereinbefore using a glass-filter with a maximum pore size of 20 microns.

The polymer can have any average molecular weight, preferably from about 1000 to 1,000,000, or even form 4000 to 250,000 or even form 10,000 to 200,000 or even form 20,000 to 75,000. Highly preferred may be polymeric material having a weight average molecular weight of from 30,000 to 70,000.

Depending on the required properties of the component herein, the polymeric material can be adjusted. For example, to reduce the solubility, polymers may be included in the material, which have high molecular weights typically above 50,000 or even above 100,000, and vice versa. For example, to change the solubility, polymers of varying level of hydrolyses may be used. For example, to improve (reduce) the elastic modulus, the cross-linking of the polymers may be increased and/or the molecular weight may be increased.

It may be preferred that the polymer used in the component herein has a secondary function, for example a function in the composition wherein component is to be incorporated. Thus, for example, for cleaning products, it is useful when the polymer in the polymeric material is a dye transfer inhibiting polymer, dispersant etc.

Preferred are polymers selected from polyvinyl alcohols and derivatives thereof, polyethylene glycols and derivatives thereof, polyvinyl pyrrolidone and derivatives thereof, cellulose ethers and derivatives thereof, and copolymers of these polymers with one another or with other monomers or oligomers. Most preferred are PVP (and derivatives thereof) and/or PEG (and derivatives thereof) and most preferably PVA (and derivatives thereof) or mixtures of PVA with PEG and/or PVP (or derivatives thereof). Most preferred may also be a polymeric material only comprising PVA. Preferably, such polymers have a level of hydrolysis of at least 50%, more preferably at least 70% or even from 85% to 95%.

Plasticiser

Any plasticiser which is suitable to aid the formation of a matrix as defined herein can be used. Mixtures of plasticiser may also be used. Preferably, when water is used, an additional plasticiser is present.

Preferably, the plasticiser or at least one of the plasticisers, has a boiling point above 40° C., preferably above 60° C., or even above 95° C., or even above 120° C., or even above 150° C.

Preferred plasticisers include glycerol or glycerine, glycol derivatives including ethylene glycol, digomeric polyethylene glycols such as diethylene glycol, triethylene glycol and tetraethylene glycol, polyethylene glycol with a weight average M.W. of below 1000, wax and carbowax, ethanolacetamide, ethanolformamide, triethanolamine or acetate thereof, and ethanolamine salts, sodium thiocyanates, ammonium thiocyanates, polyols such as 1,3-butanediol, sugars, sugar alcohols, ureas, dibutyl or dimethyl pthalate, oxa monoacids, oxa diacids, diglycolic acids and other linear carboxylic acids with at least one ether group distributed along the chain thereof, water or mixtures thereof.

The plasticiser is preferably present at a level of at least 0.5% by weight of the article, preferably by weight of the matrix, provided that when water is the only plasticiser it is present at a level of at least 3% by weight of the article, or preferably by weight of the matrix.

Preferably, the plasticiser is present at a level of 1% to 35% by weight of the article or matrix, more preferably 2% to 25% or even to 15% or even to 10% or even to 8% by weight of the article or by weight of the matrix. The exact level will depend on the polymeric material and plasticiser used, but should be such that the matrix of the article has the desired Tg. For example, when urea is used, the level is preferably 1% to 10% by weight of the matrix, while when glycerine or ethylene glycol or other glycol derivatives are used, higher levels may be preferred, for example 2% to 15% by weight of the article or matrix.

Active Ingredient

The active ingredient can be any material which is to be delivered to a liquid environment, or preferably an aqueous environment and preferably an ingredient which is active in an aqueous environment. For example, when used in cleaning compositions the component can contain any active cleaning ingredients. The component may also comprise compositions, such as cleaning composition or personal care compositions.

In particular, it is beneficial to incorporate in the component, active ingredients which are moisture sensitive or react upon contact with moisture, or solid ingredients which have a limited impact robustness and tend to form dust during handling. In particular preferred in component are active ingredients, such as enzymes, perfumes, bleaches, bleach activators, fabric softeners, fabric conditioners, surfactants, such as liquid nonionic surfactant, conditioners, antibacterial agents, brighteners, photo-bleaches and mixtures thereof.

Another active ingredient is a perhydrate bleach, such as metal perborates, metal percaronates, particularly the sodium salts Also preferred active ingredients are organic peroxyacid bleach precursor or activator compound, preferred are alkyl percarboxylic precursor compounds of the imide type include the N-,N,N$^1$N$^1$ tetra acetylated alkylene diammes wherein the alkylene group contains from 1 to 6 carbon atoms, particularly those compounds in which the alkylene group contains 1, 2 and 6 carbon atoms such as tetraacetyl ethylene diarnine (TAED), sodium 3,5,5-trimethyl hexanoyloxybenzene sulfonate (iso-NOBS), sodium nonanoyloxybenzene sulfonate (NOBS), sodium acetoxybenzene sulfonate (ABS) and pentaacetyl glucose, but also amide substituted alkyl peroxyacid precursor compounds Highly preferred active ingredient for use in the component herein are one or more enzymes. Preferred enzymes include the commercially available lipases, cutinases, amylases, neutral and alkaline proteases, cellulases, endolases, esterases, pectinases, lactases and peroxidases conventionally incorporated into detergent compositions.

Suitable enzymes are discussed in U.S. Pat. Nos. 3,519,570 and 3,533,139. Preferred commercially available protease enzymes include those sold under the tradenames Alcalase, Savinase, Primase, Durazym, and Esperase by Novo Industries A/S (Denmark), those sold under the tradename Maxatase, Maxacal and Maxapem by Gist-Brocades, those sold by Genencor International, and those sold under the tradename Opticlean and Optimase by Solvay Enzymes. Preferred amylases include, for example, α-amylases obtained from a special strain of B licheniformis, described in more detail in GB-1,269,839 (Novo). Preferred commercially available amylases include for example, those sold under the tradename Rapidase by Gist-Brocades, and those sold under the tradename Termamyl, Duramyl and BAN by Novo Industries A/S. Highly preferred amylase enzymes maybe those described in PCT/U.S. Pat. No. 9,703,635, and in WO95/26397 and WO96/23873. The lipase may be fungal or bacterial in origin being obtained, for example, from a lipase producing strain of Humicola sp., Thermomyces sp. or Pseudomonas sp. including *Pseudomonas pseudoalcaligenes* or *Pseudomas fluorescens*. Lipase from chemically or genetically modified mutants of these strains are also useful herein. A preferred lipase is derived from *Pseudomonas pseudoalcaligenes*, which is described in Granted European Patent, EP-B-0218272. Another preferred lipase herein is obtained by cloning the gene from *Humicola lanuginosa* and expressing the gene in *Aspergillus oryza*, as host, as described in European Patent Application, EP-A-0258 068, which is commercially available from Novo Industri A/S, Bagsvaerd, Denmark, under the trade name Lipolase. This lipase is also described in U.S. Pat. No. 4,810,414, Huge-Jensen et al, issued Mar. 7, 1989.

Preferred Additional Ingedients

The component of the invention preferably comprises additional ingredients which can improve the dissolution properties of the article herein.

Preferred additional ingredient which improve the dissolution of the article herein preferably comprise; a sulfonated compound such as $C_1$–$C_4$ alk(en)yl sulfonates, $C_1$–$C_4$ aryl sulfonates, di iso butyl benzene sulphonate, toluene sulfonate, cumene sulfonate, xylene sulfonate, salts thereof such as sodium salts thereof, derivatives thereof, or combinations thereof, preferably di iso butyl benzene sulphonate, sodium toluene sulfonate, sodium cumene sulfonate, sodium xylene sulfonate, and combinations thereof; and/or a $C_1$–14 $C_4$ alcohol such as methanol, ethanol, propanol such as iso-propanol, and derivatives thereof, and combinations thereof, preferably ethanol and/or iso-propanol; and/or a $C_4$–$C_{10}$ diol such as hexanediol and/or cyclohexanediol, preferably 1,6-hexanediol and/or 1,4-cyclohexanedimethanol; and/or ingredients which are capable of acting as whicking agents, such as cellulosic based ingredients, especially modified cellulose; and/or swelling agents such as clays, preferred clays are smectite clays, especially dioctahedral or trioctrahedral smectite clays, highly preferred clays are montmorillonite clay and hectorite clay, or other clays found in bentonite clay formations; and/or an effervescence system, a preferred effervescence system comprises an acid source capable of reacting with an alkali source in the presence of water to produce a gas.

The component of the invention preferably comprises additional ingredients which can improve the stability of the active ingredient of the article herein.

These additional ingredients are typically capable of stabilising the active ingredient of the component herein, this is especially preferred when the active ingredient(s) comprise an oxidative or moisture sensitive active ingredient, such as one or more enzymes. These additional ingredients may also stabilise the matrix of the component herein, and thus indirectly stabilise the active ingredient. These stabilising ingredients are defined herein as "stabilising agents".

The stabilising agent is preferably a compound which stabilises the active ingredient, or matrix, from oxidative and/or moisture degradation during storage. The stabilising agent may be, or comprise, a foam matrix stabiliser. The stabilising agent may be, or comprise, an active ingredient stabiliser, especially an enzyme stabiliser. Stabilising agents which are capable of stabilising the active ingredient indirectly by keeping the foam matrix of the article stable, herein referred to as "foam stabiliser".

Foam stabilisers preferably comprise a surfactant such as a fatty alcohol, fatty acid, alkanolamide, amine oxide, or derivatives thereof, or combinations thereof The foam stabiliser may comprise betaine, sulfobetaine, phosphine oxide, alkyl sulfoxide, derivatives thereof, or combinations thereof.

Other preferred foam stabilisers comprises one or more anions or cations such as mono, di-, tri- valent, or other multivalent metal ions, preferred are salts of sodium, calcium, magnesium, potassium, aluminium, zinc, copper, nickel, cobalt, iron, manganese and silver, preferably having an anionic counterion which is a sulphate, carbonate, oxide, chloride, bromide, iodide, phosphate, borate, acetate, citrate, and nitrate, and combinations thereof.

The foam stabiliser may comprise finely divided particles, preferably finely divided particles having an average particle size of less than 10 micrometers, more preferably less than 1 micrometer, even more preferably less than 0.5 micrometers, or less than 0.1 micrometers. Preferred finely divided particles are aluminosilicates such as zoolite, silica, or electrolytes described bereinbefore being in the form of finely divided particles.

The foam stabiliser may comprise agar—agar, sodium alginate, sodium dodecyl sulfate, polyethylene oxide, guar gum, polyacrylate, or derivatives thereof, or combinations thereof.

The foam stabiliser may be coating which is separate to the matrix of the article herein. The foam stabiliser typically partially encloses, preferably completely encloses, the article herein or the active ingredient thereof.

The coating is typically contacted to, preferable in such a manner as to form a coat on, the active ingredient prior to said active ingredient being contacted to the polymeric material or the plasticiser of the matrix, and preferably being incorporated in the article herein.

The coating may typically be contacted to, preferable in such a manner as to form a coat on, the article herein subsequent to the polymeric material and the plasticiser forming the matrix, and preferably subsequent to the active ingredient contacting said matrix or being incorporated in the article herein.

Preferred coating comprises polymers, typically selected from polyvinyl alcohols and derivatives thereof, polyethylene glycols and derivatives thereof, polyvinyl pyrrolidone and derivatives thereof, cellulose ethers and derivatives thereof, and copolymers of these polymers with one another or with other monomers or oligomers. Most preferred are PVP (and derivatives thereof) and/or PEG (and derivatives thereof) and most preferably PVA (and derivatives thereof) or mixtures of PVA with PEG and/or PVP (or derivatives thereof). These polymers do not form the matrix of the article herein. Thus, these polymers are different to the polymeric materials of the foam matrix.

A preferred coating comprises compounds such as glycerol or glycerine, glycol derivatives including ethylene glycol, digomeric polyethylene glycols such as diethylene glycol, triethylene glycol and tetraethylene glycol, polyethylene glycol with a weight average M.W. of below 1000, wax and carbowax, ethanolacetamide, ethanolformamide, triethanolamine or acetate thereof, and ethanolamine salts, sodium thiocyanates, ammonium thiocyanates, polyols such as 1,3-butanediol, sugars, sugar alcohols, ureas, dibutyl or dimethyl pthalate, oxa monoacids, oxa diacids, diglycolic acids and other linear carboxylic acids with at least one ether group distributed along the chain thereof, water or mixtures thereof These compounds do not form the foam matrix of the article herein. Thus, these compounds are different to the plastisicer of the foam matrix.

Preferred stabilising agents that are capable of stabilising the active ingredient directly, especially if said active ingredient comprises one or more enzymes, are defined herein as "active stabilisers" or "enzyme stabilisers". Typically active stabilisers interact directly with, and stabilise, the active ingredient.

Typical active stabilisers for use herein preferably comprise a surfactant. Suitable surfactants for use herein are those described hereinbefore as surfactants suitable for use as matrix stabilisers. In addition to these surfactants, other surfactants suitable for use herein may comprise surfactants such as sodium alky(en)yl sulfonates, sodium alkoxysulfonates, preferred alkoxysulfonates are those comprising from 10 to 18 carbon atoms in any conformation, preferably linear, and having an average ethoxylation degree of from 1 to 7, preferably from 2 to 5.

Other preferred active stabilisers comprise boric acid, formic acid, acetic acid, and salts thereof. These acid salts preferably comprise counerions such as calcium and/or sodium.

Preferred active stabilisers comprise cations such as calcium and or sodium. Preferably calcium chloride and/or sodium chloride.

Other preferred active stabilisers comprise small peptide chains averaging from 3 to 20, preferably from 3 to 10 amino acids, which interact with and stabilise the active ingredient, especially enzyme(s).

Other active stabilisers comprise small nucleic acid molecules, typically comprising from 3 to 300, preferably from 10 to 100 nucleotides. Typically nucleic acid molecules are deoxyribonucleic acid and ribonucleic acid. The nucleic acid molecules may be in the form of a complex with other molecules such as proteins, or may form a complex with the active ingredient of the article herein, especially enzyme(s).

Active stabilisers suitable for use herein, especially when the article herein comprises a bleach, comprise anti-oxidants and/or reducing agents such as thiosulphate, methionine, urea, thiourea dioxide, guanidine hydrochloride, guanidine carbonate, guanidine sulfamate, monoethanolamine, diethanolamine, triethanolamine, amino acids such as glycine, sodium glutamate, proteins such as bovine serum albumin and casein, tert-butylhydroxytoluene, 4-4,-butylidenebis (6tert-butyl-3-methyl-phenol), 2,2'-butlidenebis (6-tert-butyl-4-metbylphenol), (monostyrenated cresol, distyrenated cresol, monostyrenated phenol, distyrenated phenol, 1,1-bis (4-hydroxyphenyl) cyclohexane, or derivatives thereof, or a combination thereof.

Other active stabilisers may comprise a reversible inhibitor of the active ingredient. Without wishing to be bound by theory, it is believe that a reversible inhibitor of the active ingredient, especially if the active ingredient comprises one or more enzymes, may form a complex with, and improve the stability of, said active ingredient, and thus, stabilises the active ingredient during storage. When the active ingredient is released, typically into a liquid environment, the reversible inhibitor dissociates from the active ingredient and the active ingredient is then able to perform the desired action it is designed or intended to perform.

Active stabilisers suitable for use herein may comprise sugars, Typical sugars for use herein include those selected from the group consisting of sucrose, glucose, fructose, raffinose, trehalose, lactose, maltose, derivatives thereof, and combinations thereof.

The active stabiliser may also comprise sugar alcohols such as sorbitol, mannitol, inositol, derivatives thereof, and combinations thereof.

It may be preferred that the active stabiliser is in the form of a coating or barrier which at least partially encloses the article herein or the active ingredient thereof, preferably completely encloses the article herein or the active ingredient thereof, especially an enzyme.

EXAMPLES

Example 1

A Process for Preparing a Foam Component 4700 g of a 33 w/w % solution of polyvinyl alcohol (weight average molecular weight being from 30000 to 70000) is mixed with 159.3 g of glycerol and 01 9.8 g citric acid in a high shear mixer until a smooth foam is formed. This mixture is transferred to a feed tank, and is pumped, using a gear pump, into drum, known under the trade name as Rotoform supplied by Sandvik Conveyor GMBH. The drum is perforated with apertures having a size of 1000 micrometers, spaced 2500 micrometers apart. The perforated drum is positioned above a smooth surfaced drum, the shortest distance apart (the distance at the nearest point of proximity) is 1000 micrometers. The perforated drum rotates at 15 rpm whilst the mixture is pumped through the apertures of the perforated drum and onto smooth surfaced drum coated with silicone oil heated to 30° C., to form pastilles on said smooth surfaced drum. When one quarter of the smooth surfaced drum is covered by pastilles, the extrusion process is stopped and the pastilles are dried in hot air at a temperature of 70° C. until the surfaces of the pastilles are dry to touch. The resulting dried pastilles are scraped off the smooth surfaced drum and collected.

Example 2

A Process for Preparing a Foam Component 4700 g of a 33 w/w % solution of polyvinyl alcohol (weight average molecular weight being from 30000 to 70000) is mixed with 3360 g enzyme solution (5% by weight active enzyme and 85% by weight water), 159.3 g of glycerol and 155 g cyclohexane dimethanal in a high shear mixer until a smooth foam is formed. This mixture is transferred to a feed tank, and is pumped, using a gear pump, into drum, known under the trade name as Rotoform supplied by Sandvik Conveyor GMBH. The drum is perforated with apertures having a size of 1000 micrometers, spaced 2500 micrometers apart. The perforated drum is positioned above a smooth surfaced drum, the shortest distance apart (the distance at the nearest point of proximity) is 1000 micrometers. The perforated drum rotates at 15 rpm whilst the mixture is pumped through the apertures of the perforated drum and onto smooth surfaced drum coated with silicone oil heated to 30° C., to form pastilles on said smooth surfaced drum. When one quarter of the smooth surfaced drum is covered by pastilles, the extrusion process is stopped and the pastilles are dried in hot air at a temperature of 70° C. until the surfaces of the pastilles are dry to touch. The resulting dried pastilles are scraped off the smooth surfaced drum and collected.

Example 3

A Process for Preparing a Foam Component

A 4000 g solution is prepared by mixing 1464.0 g of polyvinyl alcohol (weight average molecular weight being from 30000 to 70000) 2282.0 g enzyme solution (5% by weight active enzyme and 85% by weight water), 150.4 g of glycerol and 103.6 Sodium Thiosulphate in a high shear mixer until a smooth foam is formed. This mixture is transferred to a feed tank, and is pumped, using a gear pump, into a drum, known under the trade name as Rotoform supplied by Sandvik Conveyor GMBH. The drum is perforated with apertures having a size of 300 micrometers, spaced 100 micrometers apart. The perforated drum is positioned above a smooth surface steel belt conveyor. The perforated drum rotates at 100 rpm whilst the mixture is pumped through the aperture of the perforated drum and onto smooth surfaced steel belt conveyor coated with silicone oil heated to 30° C., to form pastilles on said smooth surfaced belt. When the entire length of the smooth surface steel conveyor belt is covered by pastilles, the extrusion process is stopped and the pastilles are dried in hot air at a temperature of 70° C. until the surfaces of the pastilles are dry to touch. The resulting dried pastilles are scraped off the smooth surfaced drum and collected.

Example 4

A Process for Preparing a Foam Component

A 4000 g solution is prepared as described in example 3 with the exception of having $CO_2$ gas dissolved into the solution. The $CO_2$ dissolution is achieved by placing the described solution into a 10 L pressure vessel, and charging the pressure vessel with $CO_2$ gas until a pressure of 1.0 bar is achieved. The $CO_2$ feed is stopped at this point, and the pressure vessel and its contents area allowed to reach dissolution equilibrium. This mixture is pumped directly from the pressure vessel, using a gear pump, into a drum, known under the trade name as Rotoform supplied by Sandvik Conveyor GMBH. The drum is perforated with apertures having a size of 300 micrometers, spaced 100 micrometers apart. The perforated drum is positioned above a smooth surface steel belt conveyor. The perforated drum rotates at 100 rpm whilst the mixture is pumped through the apertures of the perforated drum and onto smooth surfaced steel belt conveyor coated with silicone oil to form pastilles on said smooth surfaced belt. The steel belt conveyor is sprayed with a cooling media on the side opposite the side where the pastilles are formed. The cooling media spray results in a belt temperature of −10° C. which immediately sets the pastilles. The pastilles are removed from the smooth surface steel belt, optionally with the aid of a scraper blade. Upon removal, the pastilles fall via gravity, or are similarly transported, to a Fluid Bed Dryer/Coater where moisture removal can take place. Furthermore, an additional coating can be applied in the Fluid Bed Dryer/Coater. The resulting dried, coated pastilles are removed from the Fluid Bed Dryer/Coater.

What is claimed is:

1. A process for preparing a foam component, said process comprising the steps of extruding a viscous mixture through an aperture of a rotating extrusion plate, onto a receiving surface; wherein a gas is incorporated into said viscous mixture either prior to, simultaneous to, or subsequent to, extrusion of said viscous mixture through said aperture.

2. The process according to claim 1, wherein said viscous mixture comprises a viscosity of from about 25 mPas to 20000 mPas.

3. The process according to claim 1, wherein the distance between said extrusion plate and said receiving surface is at least 50 micrometers.

4. The process according to claim 1, wherein said aperture comprises a size of from about 50 micrometers to about 3000 micrometers.

5. The process according to claim 1, wherein said viscous mixture comprises a water content of from about 0.1% to about 80% by weight.

6. The process according to claim 1, wherein the direction of rotation of the rotating extrusion plate is perpendicular to the direction of flow of the viscous liquid through the aperture of said rotating plate.

7. The process according to claim 1, wherein said viscous mixture comprises a member selected from the group consisting of: polymeric material, plasticiser, active ingredient, dissolution aid, stability aid and combinations thereof.

8. The process according to claim 1, wherein said viscous mixture is extruded through said aperture at a temperature of from about 0° to about 50° C.

9. The process according to claim 1, wherein said aperture comprises a shape selected from the group consisting of: diamond, square, circle, triangle and combinations thereof.

10. The process according to claim 1, wherein said gas comprises an element selected from the group consisting of: dioxide, nitrogen and combinations thereof.

11. The process according to claim 1, wherein said rotating extrusion plate rotates at a speed of about 1 rpm to about 1000 rmp.

12. The process according to claim 1, wherein the rotating extrusion plate comprises a tip speed of about 0.1 ms—1 to about 1600 ms—1.

13. The process according to claim 1, wherein said receiving surface and/or rotating extrusion plate is at least partially coated with a release agent.

14. The process according to claim 1, wherein said foam component is water-soluble or water-dispersible.

15. A method of using the process according to claim 1, to prepare a foam component suitable for use in cleaning compositions, fabric care composition, personal care compositions, cosmetic compositions, pharmaceutical compositions.

16. The method according to claim 15, wherein said method further comprises the step of incorporating an active ingredient into said foam component, said active ingredient selected from the group consisting of: enzymes, perfumes, surfactants, brighteners, dyes, suds suppressors, bleaches, bleach activators, fabric softeners, antibacterial agents, effervescing systems and mixtures thereof.

* * * * *